United States Patent
Ireland

(10) Patent No.: US 6,528,696 B1
(45) Date of Patent: Mar. 4, 2003

(54) PLIABLE CONTACT BANDAGE

(76) Inventor: Christine M. Ireland, 6 Savona Drive, Toronto, Ontario (CA), M8W 4V1

(*) Notice: Subject to any disclaimer, the term of this patent is extended or adjusted under 35 U.S.C. 154(b) by 155 days.

(21) Appl. No.: 09/480,946

(22) Filed: Jan. 11, 2000

(51) Int. Cl.$^7$ .................................................. A61F 13/00
(52) U.S. Cl. ............................ 602/41; 602/2; 604/358; 604/387; 604/389; 607/108; 607/114
(58) Field of Search ..................................... 602/2, 14, 41, 602/54, 5, 13, 60, 63; 128/882, 878, 879; 604/358, 387, 389; 607/108, 114

(56) References Cited

U.S. PATENT DOCUMENTS

| | | |
|---|---|---|
| 4,081,150 A | 3/1978 | Tyson |
| 4,190,054 A | 2/1980 | Brennan |
| 4,326,533 A * | 4/1982 | Henderson |
| 4,669,476 A | 6/1987 | Gordon et al. |
| 5,052,387 A | 10/1991 | Natali |
| 5,150,707 A * | 9/1992 | Anderson |
| 5,310,400 A | 5/1994 | Rogers et al. |
| 5,324,318 A | 6/1994 | Smith |
| 5,409,500 A | 4/1995 | Dyrek |
| 5,697,962 A | 12/1997 | Brink et al. |
| 5,766,235 A | 6/1998 | Kostopoulos |
| 5,887,437 A | 3/1999 | Maxim |

* cited by examiner

Primary Examiner—Denise M. Pothier
Assistant Examiner—Lalita M Hamilton
(74) Attorney, Agent, or Firm—Marks & Clerk

(57) ABSTRACT

A pliable contact bandage for placement over a wound site located on any skin surface, is provided. The apparatus includes a re-openable, flexible enclosure adapted to receive a source of heat or cold, and an adhesive for mounting the pliable contact bandage on a skin surface. The source of heat or cold is temporarily placed within the flexible enclosure and the pliable contact bandage is placed over the wound site in a heat conducting relationship. Typically, a hypo-allergenic adhesive is located along at least a portion of the periphery of the flexible enclosure. The periphery of the flexible enclosure surrounds the wound site.

20 Claims, 2 Drawing Sheets

PLIABLE CONTACT BANDAGE

FIELD OF THE INVENTION

This invention relates to the field of therapeutic bandages for application at a wound site. In particular, this invention relates to a device which may be mounted on a skin surface and so as to apply heat or cold to the wound site.

BACKGROUND OF THE INVENTION

The use of hot and cold packs as a means to provide therapy to a wound site on the skin surface is well known in the art. They are commonly used as a treatment for sport injuries, post-surgery, and chronic pain. Conventionally, a cold pack is used to reduce swelling and bruising and a hot pack is used to sooth pulled muscles or strains. These packs may be chemically activated or contain either ice or hot water. They are typically applied at the wound site and held in place by an elasticized bandage, they may simply be held by the hand of the person receiving the treatment. When the pack is held in place by the patient, it may be applied intermittently as is generally recommended by medical practitioners. A hand held pack however is inconvenient for periods of extended use and restricts the mobility of the user. However, when using an elasticized bandage to hold the pack in place, the patient must continually wrap and unwrap the bandage so as to apply the pack intermittently. Furthermore, while an elasticized bandage is easy to apply to major muscle groups and commonly injured areas, wound sites on the face for example would not facilitate the application of a hot or cold pack unless it was hand held.

The prior art has expanded to attempt to overcome these difficulties. Support bandages intended to wrap around a limb and having at least one pouch which may contain a removable cold pack are presently available; however, such devices are not applicable for use on all portions of the body. A cold pack with a self adhering surface such that it may be attached to any skin surface overcomes one limitation of the prior art; however, placing an adhesive over or adjacent a wound site is not applicable for all types of injuries. There is also the problem of trauma to the skin surrounding the wound site if a bandage (usually a new bandage each time) is continually applied and removed.

Typically, it is considered that the medical efficacy of continued periodic application of either cold or heat to a wound site for a period of longer than 24 hours is lost. However, for a period of up to 24 hours, there may be a continuing requirement for periodic application of cold or heat, but not continuous application, to a wound site. Thus, the present invention serves those needs, by providing an apparatus that can remain stationary on the patient's body at a wound site, while permitting periodic application of cold or heat to the wound, without the risk of needless trauma to the skin surrounding the wound site, and the excoriation caused thereby, as a consequence of repeatedly applying and removing an adhesive bandage.

DESCRIPTION OF THE PRIOR ART

U.S. Pat. No. 4,081,150 issued to TYSON teaches a multi-purpose therapeutic pad which has a pouch to permit the application of heat or cold when the device is applied. The pad is wrapped around the injured area so as to apply heat or cold to the injury. The pad is fastening in place by a series of Velcro fastening means.

U.S. Pat. No. 4,190,054 issued to BRENNAN teaches a therapeutic bandage with removable hot or cold packs. The bandages are made from an elastic material and are typically used following a surgery to hold the flesh of the body part firmly in place. The bandage has a series of attachment points on the outer surface which may receive hot or cold packs. The bandage wraps around the body part where the wound site is located and is fastened by a plurality of Velcro strips.

U.S. Pat. No. 4,669,476 issued to GORDON and ZABROWSKY teaches a compression bandage having cold application properties. The bandage comprises an elongated plastic strip which wraps around the injured portion of the user's body and applies compression to the wound site. There is an opening at one end of the bandage such that a removable cold pack maybe inserted therein, however, to view the injured area, the bandage must be removed. Fasteners located at the open end hold the cold pack in place when in use.

U.S. Pat. No. 5,502,387 issued to NATALI teaches a cold pack for wrapping an injured limb and a method of making the same. The cold pack is constructed from two sheets of thermoplastic polyethylene which form a rectangular shape. At one end of the shorter side of the rectangle, a small ice compartment is formed, at the opposing end, there is an adhesive strip. The bandage is wrapped around an injured limb such that the ice pack is in contact with the injured area and the bandage is held in place around the limb by the adhesive strip.

U.S. Pat. No. 5,310,400 issued to ROGERS and HAMMOND teaches a therapeutic bandage that is readily removable and having an internal air bladder that may provide compression to the injury, and an internal coolant bladder that applies cold to the injured area.

U.S. Pat. No. 5,324,318 issued to KIRBY teaches a cold compress system. The apparatus includes a flexible application bag which may be wrapped around the injured area, and a supply container. The supply container is elevated above the application bag such that the liquid cold may flow by gravity from the supply container to the application bag. As the application bag is filled with the liquid cold it applies pressure to the injured area.

U.S. Pat. No. 5,409,500 issued to DYREK teaches a versatile therapeutic cold pack. The cold pack comprises a plurality of compartments hinged together along intersecting axes. Each of these compartments contains a refrigerant gel which, when cooled, absorbs large quantities of heat. The compartments are adapted to be folded with respect to one another such that they fit closely against an irregularly shaped anatomical surface. Different configurations of the compartments accommodate various body parts. The cold pack is placed over the wound site and wraps around the majority of the surrounding area and is secured by elastomeric straps having velcro fasteners.

U.S. Pat. No. 5,697,962 issued to BRINK and GIBSON teaches a therapeutic wrap having one or more chambers accessible for placement of a hot or cold pack therewithin without disconnecting the wrap. In order to view the injured area or wound site to assess progress or the effects of the application of heat or cold, the wrap must be removed from the user.

U.S. Pat. No. 5,766,235 issued to KOSTOPOULOS teaches an apparatus which provides cooling to a human body. The apparatus comprises a shallow pouch having a closeable flap and a strap. The pouch is adapted to receive a cooling pack therein and the flap has a plurality of fasteners configured so as to releasably fasten the flap in a closed position. The strap wraps around a human wrist and positions the cooling pack against the inside of the wrist.

U.S. Pat. No. 5,887,437 issued to MAXIM teaches a self-adhering cold pack. The cold pack defines a sealed envelope that allows for the positioning of a cooling agent within the cold pack volume. There is a bandage sheet fixed to the envelope which extends beyond the envelopes outer perimeter to form mounting tabs. A hypo-allergenic bandage adhesive covers the bandage sheet and the mounting tabs such that the envelope may be mounted on a skin surface of the user and covers the entirety of the injured area. In order to view the wound site, the adhesive bandage must be peeled away from the skin of the user. This process lessens the effectiveness of the adhesive and may require the application of a new bandage each time after removing the bandage from the injured site. Repeated removal and re-application may irritate the skin of the user and in some cases may cause second degree burns.

SUMMARY OF THE INVENTION

In accordance with one aspect of the present invention, there is provided pliable contact bandage for placement over a wound site, where the wound site may be on any skin surface. The pliable contact bandage comprises a re-openable flexible enclosure being adapted to receive a source of heat or cold, and adhesive means for mounting the pliable contact bandage to a skin surface. The periphery of the pliable contact bandage surrounds the wound site and the adhesive means is located along at least a portion of the periphery of the pliable contact bandage.

In a particular embodiment of the present invention, the flexible enclosure is a re-openable pouch having an outer periphery and an open end. The adhesive means are permanently affixed to at least a portion of the outer periphery of the pouch. Fastening means are located at the open end of the pouch.

In another particular embodiment of the present invention, the flexible enclosure comprises a re-openable pouch having an outer edge and an open end, and an outer peripheral structure. The pouch is fixedly attached to at least a portion of the peripheral structure so as to permit the pouch to be removed away from the peripheral structure, and in turn, expose the wound site, while remaining part of the pliable contact bandage. The flexible enclosure is adjacent to the wound site. The outer edge of the lower side of the re-openable pouch facing the wound site is removably attached to a portion of the peripheral structure. Fastening means are located at the open end of the pouch.

In an additional particular embodiment of the present invention, the flexible enclosure comprises a re-openable pouch having an open end, and an outer peripheral structure. The pouch is affixed temporarily to the peripheral structure such that it may be removed at any instant in time the pouch may be completely removed from the peripheral structure. When a source of heat or cold is placed within the pouch and, is in turn, positioned in a heat conducting relationship with the wound site, the source of heat or cold may be removed from the wound site with the removal of the pouch from the peripheral structure. Fastening means are located at the open end of the pouch.

In a fourth particular embodiment of the present invention, the flexible enclosure comprises a re-openable pouch having an open end, an upper surface, a lower surface, and fastening means, and an outer peripheral structure. The fastening means are located on the outer edges of the upper and lower surfaces of the pouch and where the upper and lower surfaces are adjacent to one another when the flexible enclosure is placed in a heat conducting relationship with the wound site. The upper surface of the pouch may be removed away from the lower surface of the pouch by release of the fastening means. The flexible enclosure, when adjacent to the wound site and the outer edge of the lower side of the re-openable pouch faces the wound site, is removably attached to at least a portion of the peripheral structure.

The fastening means for each embodiment facilitate the pouch being re-openable. The fastening means may be typically one of the following: hook and loop fasteners, snaps, buttons, zippers, interlocking bead and groove, and combinations thereof.

The means for the removable attachment of the re-openable pouch to the peripheral structure in particular embodiments may typically be one of the following: hook and loop fasteners, snaps, buttons, zippers, interlocking bead and groove and combinations thereof.

The pliable contact bandage has at least the lower surface of the interior of the flexible enclosure preferably made from terry cloth, to absorb condensation and act as an insulating layer.

The adhesive means of the pliable contact bandage surrounds the entire periphery of the bandage. The adhesive means may have a series of inwardly directed slits so as to enhance the mobility of the user and allow the pliable contact bandage to better conform with the shape of the body where the wound site is located.

The adhesive means of the pliable contact bandage may also comprise a plurality of outwardly directed, spaced apart, adhesive, hypo-allergenic strips.

Typically, the adhesive means of the pliable contact bandage has a quick release backing.

The source of heat or cold placed within the flexible enclosure is pliable so as to conform with the shape of the body where the wound site is located. Typically, a heat or cold source may be chemically activated such that when the separate reactive chemicals are combined, they undergo either an endothermic reaction and provide cooling or an exothemeric reaction and produce heat. The cooling or heating agent may also be in, some instances, mainly water. When cold source is desired, ice may also be used.

In general, the pliable contact bandage of the present invention is disposable.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

Figure 1:
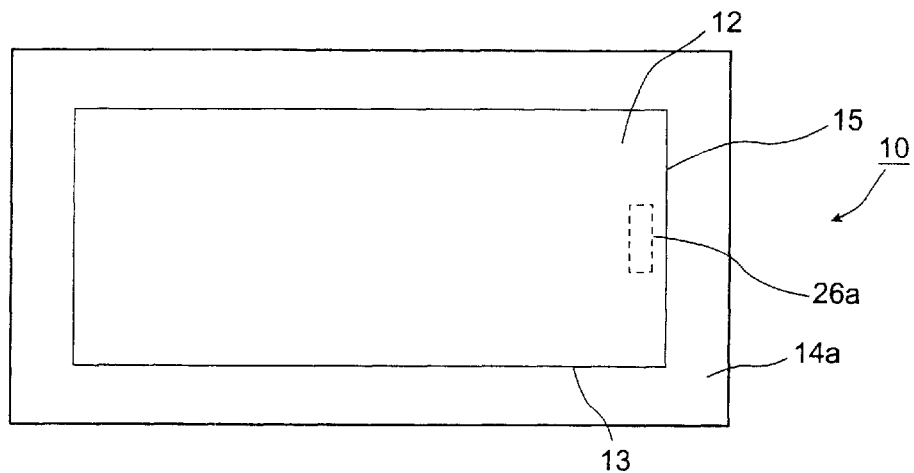
FIG. 1 is a top view of a pliable contact bandage in keeping with the present invention.

DETAILED DESCRIPTION OF THE PREFERRED EMBODIMENTS:

Referring now to the drawings, there is illustrated a pliable contact bandage for placement over a wound site, generally designated by reference numeral 10. The pliable contact bandage 10, shown in general configuration in FIG. 1, comprises a re-openable flexible enclosure 12 and adhesive means 14a. The re-openable flexible enclosure 12 is adapted to receive a source of heat or cold (not shown) which may be temporarily placed within the enclosure 12, such that it is in a heat conducting relationship over the wound site. The adhesive means 14a is located along at least a portion of the periphery 13 of the flexible enclosure 12 where the periphery 13 of the flexible enclosure 12 surrounds the wound site. In a first particular embodiment shown in FIG. 1, the flexible enclosure is a pouch 12 having and outer periphery 13 and a open end 15. The adhesive means 14a are permanently affixed to at least a portion of the outer periphery 13 of the pouch 12 and fastening means 26a are located at the open end 15 of the pouch 12.

Figure 2:
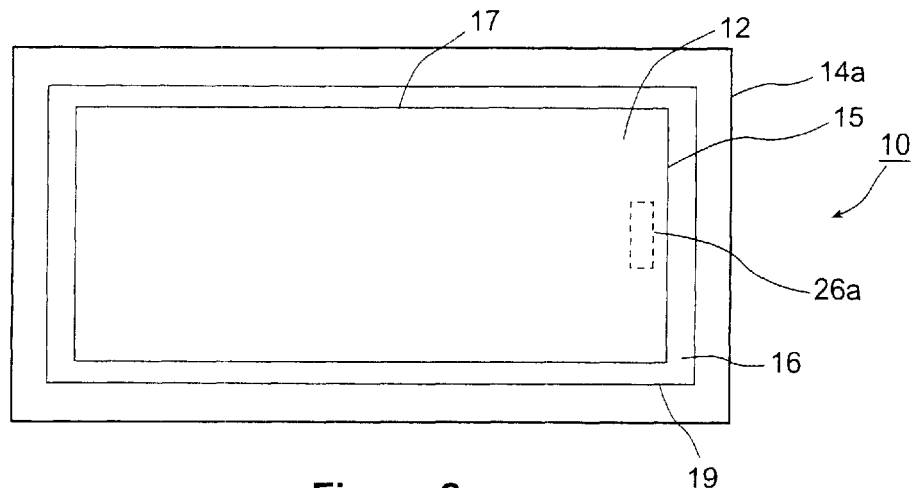
FIG. 2 is a top view of another particular embodiment of a pliable contact bandage in keeping with the present invention.
Figure 5:
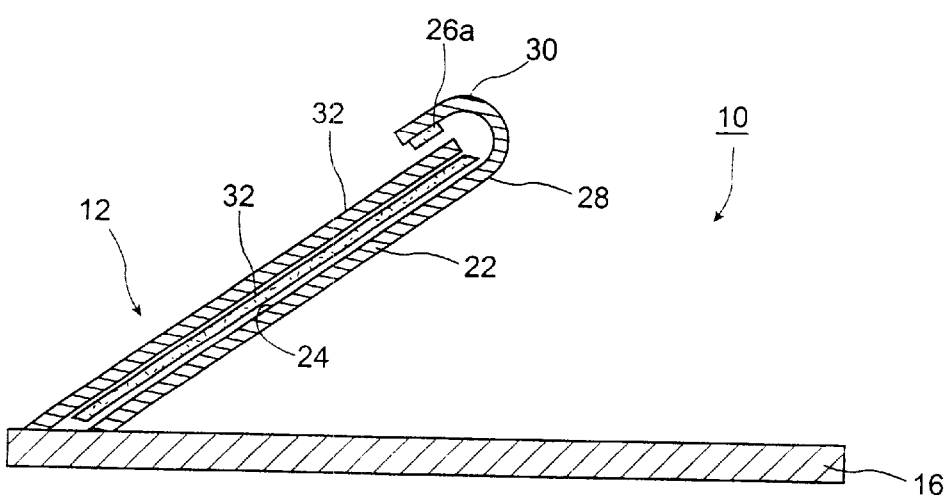
FIG. 5 is a side view of a typical pliable contact bandage in keeping with the present invention.

FIG. 2 shows another particular embodiment of the pliable contact bandage 10. In this instance, the flexible enclosure comprises an outer peripheral structure 16 and a re-openable pouch 12 having an outer edge 17 and an open end 15. The pouch 12 is fixedly attached to at least a portion of the peripheral structure 16 so as to permit the pouch 12 to be removed away from the peripheral structure 16, and in turn, expose the wound site, while remaining part of the pliable contact bandage 10. The flexible enclosure, when in use, is adjacent to the wound site. The outer edge 17 of the lower side (not shown) of the pouch 12 facing the wound site is removably attached (as shown in FIG. 5) to a portion of the peripheral structure 16. The means for the removable attachment 18a of the pouch 12 to the peripheral structure 16 is typically one of hook and loop fasteners, snaps, buttons, and combinations thereof. Fastening means 26a are located at the open end 15 of the pouch 12.

In another particular embodiment the flexible enclosure comprises an outer peripheral structure 16 and a re-openable pouch 12 having an open end 15. The pouch 12 is temporarily affixed by temporary attachment means 18a, 18b to the peripheral structure 16 such that, at any instant in time, the pouch 12 may be completely removed from the peripheral structure. When a source of heat or cold is placed with the pouch 12 and is in turn, positioned over the wound site so as to be in a heat conducting relationship, the source of heat or cold (not shown) may be completely removed from the wound site by the removal of the pouch 12 from the peripheral structure 16. Fastening means 26a are located at the open end 15 of the pouch 12.

Figure 3:
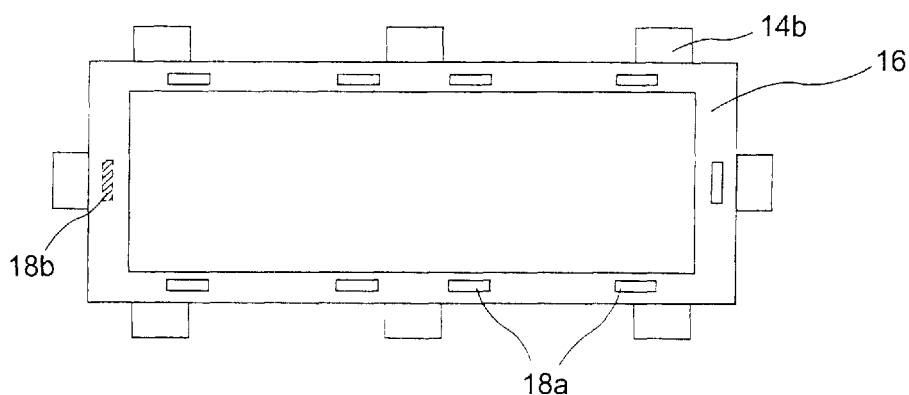
FIG. 3 is a top view of the peripheral structure of a typical pliable contact bandage in keeping with the present invention.

FIG. 3 shows a top view of the peripheral structure 16 described in the above embodiment.

The adhesive means 14b located on the outer edge 19 of the peripheral structure 16, as shown in FIG. 3, comprise a plurality of outwardly directed, spaced apart, adhesive, hypo-allergenic strips. Adhesive means 14a may surround the entire periphery of the flexible enclosure, as shown in FIG. 1. To enhance the mobility of the user and better facilitate the attachment of the pliable contact bandage 10 to a skin surface, the adhesive means 14a may have a series of inwardly directed slits. The adhesive means 14a, 14b may have a quick release backing.

Figure 4:
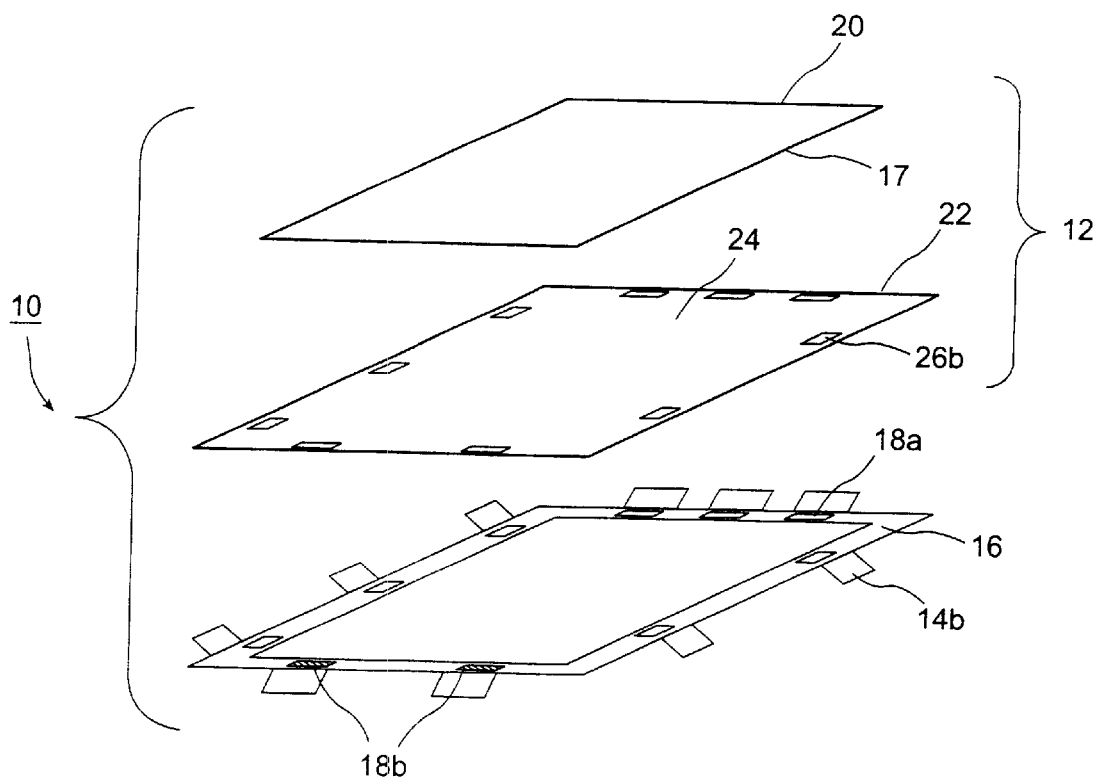
FIG. 4 is an exploded view of another particular embodiment of a pliable contact bandage in keeping with the present invention.

FIG. 4 is a perspective view of another particular embodiment of the pliable contact bandage 10. The flexible enclosure comprises a re-openable pouch 12 having an upper surface 20, a lower surface 22, and fastening means 26b, and a peripheral structure 16. The flexible enclosure, when adjacent to the wound site, is removably attached 18a, 18b to at least a portion of the peripheral structure. The fastening means 26b are located on at least a portion of the outer edge 17 of the upper surface 20 and the lower surface 22 of the pouch 12 such that they are in an opposing relationship. The upper surface 20 and the lower surface 22 are adjacent to one another, and the fastening means 26b engaged, when the flexible enclosure is placed in a heat conducting relationship with the wound site. The upper surface 20 of the pouch 12 may be removed away from the lower surface 22 of the pouch 12 by release of the fastening means 26b.

The fastening means 26a, 26b for each embodiment facilitate the pouch 12 being re-openable. The fastening means 26a, 26b, are typically on of the following: hook and loop fasteners, snaps, buttons, and combinations thereof.

The top side 24 of the lower surface 22 of the interior of the pouch 12 may be constructed from terrycloth to absorb condensation and act as an insulating layer.

The pliable contact bandage 10 is disposable, and thus intended for only a single use.

A heat or cold pack 32 contained within the flexible enclosure is self-contained and pliable so as to conform with the shape of the body where the wound site is located.

The pliable contact bandage 10 of the present invention, when in use is placed adjacent to the wound site, and is fixedly attached to the area surrounding the wound site by the adhesive means 14a, 14b. In at least one embodiment, the peripheral structure 16 surrounds the wound site and is configured such that it allows the injured area to be visible when the re-openable pouch 12 is removed away from the peripheral structure. The pliable contact bandage 10, in keeping with the present invention allows for the examination of the injured area while the pliable contact bandage is fixedly attached to the skin surface surrounding the wound site. This key feature prevents the need to continually remove a therapeutic bandage covering the wound site in order to visibly access the healing process and the effectiveness of the treatment being applied. In addition, the constant stress placed on the skin surrounding the wound site by the frequent removal and re-application of an adhesive may cause second degree burns.

Still further, the pliable contact bandage 10 of the present invention is adaptable for placement on any skin surface and does not require any additional securing means i.e. straps that wrap around a limb or joint to hold the bandage or therapeutic cold pack in place.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element.

What is claimed is:

1. A pliable contact bandage for placement over a wound site, wherein said wound site may be on any skin surface; said pliable contact bandage comprising:
a re-openable, flexible enclosure being adapted to receive a source of heat or cold which may be temporarily placed therewithin, so as to be in heat conducting relationship over the wound site; and a means for the removable attachment of said pouch to said peripheral structure;
adhesive means for mounting of said pliable contact bandage to a skin surface;
wherein said adhesive means is located along the periphery of said pliable contact bandage; and wherein the periphery of said pliable contact bandage surrounds the wound site during;
wherein said flexible enclosure comprises an outer peripheral structure and a pouch having an outer edge and an open end,
wherein said pouch is fixedly attached to at least a portion of said peripheral structure so as to permit said pouch to be removed away from said peripheral structure exposing the wound site, while remaining part of the pliable contact bandage;
wherein, when said flexible enclosure is adjacent to the wound site, said outer edge of the lower side of said pouch facing the wound site is removably attached to a portion of said peripheral structure; and
wherein fastening means is located at said open end of said pouch.

2. The pliable contact bandage of claim 1, wherein said flexible enclosure is a re-openable pouch having an outer periphery and an open end said adhesive means being permanently affixed to at least a portion of said outer periphery of said pouch.

3. The pliable contact bandage of claim 1, wherein said fastening means facilitates said pouch being re-openable and is chosen from the group consisting of hook and loop fasteners, snaps, buttons, and combinations thereof.

4. The pliable contact bandage of claim 1, wherein the means for the removable attachment of said pouch to said peripheral structure is chosen from the croup consisting of hook and loop fasteners, snaps, buttons, and combinations thereof.

5. The pliable contact bandage of claim 1, wherein at least the lower surface of the interior of said flexible enclosure is terrycloth, so as to absorb condensation and act as an insulating layer.

6. The pliable contact bandage of claim 1, wherein said adhesive means surrounds the entire periphery of the pliable contact bandage.

7. The pliable contact bandage of claim 1, wherein said adhesive means comprises a plurality of outwardly directed, spaced apart, adhesive, hypo-allergenic strips.

8. The pliable contact bandage of claim 1, wherein said adhesive means surrounds the entirety of the peripheral edge of said flexible enclosure and has a series of inwardly directed slits.

9. The pliable contact bandage of claim 1, wherein said adhesive means has a quick release backing.

10. The pliable contact bandage of claim 1, wherein said source of heat or cold is self contained and pliable so as to conform with the shape of the body where the wound site is located.

11. The pliable contact bandage of claim 1, wherein, when said pliable contact bandage is affixed to the skin surface, the mobility of the user in not limited.

12. The pliable contact bandage of claim 1, wherein said pliable contact bandage is disposable.

13. A pliable contact bandage for placement over a wound site, wherein said wound site may be on any skin surface; said pliable contact bandage comprising:
a re-openable, flexible enclosure being adapted to receive a source of heat or cold which may be temporarily placed therewithin, so as to be in heat conducting relationship over the wound site; and a means for the removable attachment of said pouch to said peripheral structure;
adhesive means for mounting of said pliable contact bandage to a skin surface;
wherein said adhesive means is located along the periphery of said pliable contact bandage; and wherein the periphery of said pliable contact bandage surrounds the wound site during;
wherein said flexible enclosure comprises an outer peripheral structure and a pouch having an open end; said pouch being temporarily affixed to said peripheral structure;
wherein, when a source of heat or cold is placed within said pouch and is in a heat conducting relationship with the wound site, at any instant in time said pouch may be completely removed from said peripheral structure so as to also remove the source of heat or cold from the wound site; and
wherein fastening means is located at said open end of said pouch.

14. The pliable contact bandage of claim 13, wherein said fastening means facilitates said pouch being re-openable and is chosen from the group consisting of hook and loop fasteners, snaps, buttons, and combinations thereof.

15. The pliable contact bandage of claim 13, wherein, when said flexible enclosure is adjacent to the wound site, the outer edge of the lower side of said pouch which faces the wound site is removably attached to at least a portion of said peripheral structure.

16. The pliable contact bandage of claim 15, wherein the means for the removable attachment of said pouch to said peripheral structure is chosen from the group consisting of hook and loop fasteners, snaps, buttons, and combinations thereof.

17. The pliable contact bandage of claim 13, wherein said flexible enclosure is a re-openable pouch having an outer periphery and an open end; said adhesive means being permanently affixed to at least a portion of said outer periphery of said pouch.

18. A pliable contact bandage for placement over a wound site, wherein said wound site may be on any skin surface; said pliable contact bandage comprising:
a re-openable, flexible enclosure being adapted to receive a source of heat or cold which may be temporarily placed therewithin, so as to be in heat conducting relationship over the wound site; and
adhesive means for mounting of said pliable contact bandage to a skin surface;
wherein said adhesive means is located along the periphery of said pliable contact bandage, and wherein the periphery of said pliable contact bandage surrounds the wound site during;
wherein said flexible enclosure comprises an outer peripheral structure and a pouch; said pouch having an upper surface, a lower surface and fastening means; wherein said fastening means are located on the outer edges of said upper and lower surfaces; wherein said upper surface and said lower surface are adjacent to one another when said flexible enclosure is placed in a heat conducting relationship with the wound site; and wherein said upper surface may he removed away from said lower surface of said pouch by release of said fastening means; a means for the removable attachment of said pouch to said peripheral structure.

19. The pliable contact bandage of claim 18, wherein said fastening means facilitates said pouch being re-openable and is chosen from the group consisting of hook and loop fasteners, snaps, buttons, and combinations thereof.

20. The pliable contact bandage of claim 18, wherein said flexible enclosure is a re-openable pouch having an outer periphery and an open end; said adhesive means being permanently affixed to at least a portion of said outer periphery of said pouch; and wherein fastening means is located at said open end of said pouch.

* * * * *